(12) United States Patent
Clausen

(10) Patent No.: US 8,206,944 B2
(45) Date of Patent: *Jun. 26, 2012

(54) DRY STICK DEVICE CONSTRUCTION AND METHOD FOR DETERMINING AN ANALYTE IN A SAMPLE USING SAID DRY STICK DEVICE

(75) Inventor: Kim Clausen, Tollose (DK)

(73) Assignee: Lattec I/S, Hillerod (DK)

( * ) Notice: Subject to any disclaimer, the term of this patent is extended or adjusted under 35 U.S.C. 154(b) by 917 days.

This patent is subject to a terminal disclaimer.

(21) Appl. No.: 12/161,479

(22) PCT Filed: Jan. 19, 2007

(86) PCT No.: PCT/DK2007/050004
§ 371 (c)(1),
(2), (4) Date: Sep. 4, 2008

(87) PCT Pub. No.: WO2007/082544
PCT Pub. Date: Jul. 26, 2007

(65) Prior Publication Data
US 2011/0039290 A1 Feb. 17, 2011

Related U.S. Application Data

(60) Provisional application No. 60/759,953, filed on Jan. 19, 2006.

(30) Foreign Application Priority Data

Jan. 19, 2006 (DK) .................. 2006 00084

(51) Int. Cl.
*C12Q 1/32* (2006.01)
*C12M 1/34* (2006.01)
*D05B 93/00* (2006.01)
*B29C 65/00* (2006.01)
*B32B 7/08* (2006.01)
*B32B 37/00* (2006.01)
*G01N 15/06* (2006.01)
*G01N 33/06* (2006.01)

(52) U.S. Cl. ......... 435/26; 435/287.9; 112/402; 156/60; 156/93; 156/278; 422/68.1; 436/23

(58) Field of Classification Search .......... 435/26, 435/287.9; 112/402; 156/60, 93, 278; 422/68.1; 436/23
See application file for complete search history.

(56) References Cited

U.S. PATENT DOCUMENTS

| 3,418,079 A | 12/1968 | Hans-Georg et al. |
| 3,547,780 A | 12/1970 | Finnerty et al. |
| 3,867,259 A | 2/1975 | Forgione |
| 3,875,013 A | 4/1975 | Manautou et al. |
| 3,901,657 A | 8/1975 | Lightfoot |
| 3,968,011 A | 7/1976 | Manautou et al. |
| 4,215,995 A | 8/1980 | Turk et al. |
| 4,438,067 A | 3/1984 | Siddiqi |
| 4,454,094 A | 6/1984 | Bjorling et al. |
| 4,506,019 A | 3/1985 | Lee |
| 4,710,458 A | 12/1987 | Maines |
| 4,732,736 A | 3/1988 | Kobayashi et al. |
| 4,959,305 A | 9/1990 | Woodrum |
| 5,219,730 A | 6/1993 | Potocnjak et al. |
| 5,260,219 A | 11/1993 | Fritz |
| 5,352,411 A | 10/1994 | Khuri |
| 5,370,994 A | 12/1994 | Stewart et al. |
| 5,663,054 A | 9/1997 | Williams et al. |
| 5,697,326 A | 12/1997 | Mottram et al. |
| 5,698,083 A | 12/1997 | Glass |
| 5,932,431 A | 8/1999 | Williams et al. |
| 2003/0073073 A1 | 4/2003 | Wolde-Mariam |
| 2004/0219694 A1 | 11/2004 | Chittock et al. |
| 2005/0260695 A1 | 11/2005 | Fleming et al. |

FOREIGN PATENT DOCUMENTS

| DK | PA1986 04261 | 9/1985 |
| EP | 0282192 | 9/1988 |
| EP | 0325449 | 7/1989 |
| EP | 0354978 | 2/1990 |
| EP | 0458231 | 11/1991 |
| EP | 0577092 | 1/1994 |
| EP | 0810290 | 12/1997 |
| EP | 0810436 | 12/1997 |
| EP | 0902287 | 3/1999 |
| EP | 0990706 | 9/2002 |
| EP | 1544619 A2 | 6/2005 |
| FR | 2191734 A | 2/1974 |
| GB | 2207245 | 1/1989 |
| WO | 90/12487 | 11/1990 |
| WO | 92/21980 | 12/1992 |
| WO | 93/03053 | 2/1993 |
| WO | 95/25282 | 9/1995 |
| WO | 97/17375 | 5/1997 |
| WO | 00/33074 | 6/2000 |
| WO | 02/22854 | 3/2002 |
| WO | 0222854 A2 | 3/2002 |
| WO | 03/023051 | 3/2003 |
| WO | 03023051 A2 | 3/2003 |
| WO | 03/093788 | 11/2003 |
| WO | 03093788 A2 | 11/2003 |
| WO | 2004/025301 | 3/2004 |
| WO | 2004025301 A1 | 3/2004 |

OTHER PUBLICATIONS

European Search Report for International Application No. PCT/DK2007050004 dated Dec. 11, 2008. Lippenheide et al. "Determination of Lactate Dehydrogenase Activity and Urea Content in Milk by Dry Chemistry". J. Vet. Med. A. 42. 221-225 (1995).
U.S. Appl. No. 12/161,561, filed Jul. 18, 2008.

*Primary Examiner* — Herbert J Lilling
(74) *Attorney, Agent, or Firm* — Stephen A. Bent; Foley & Lardner LLP

(57) ABSTRACT

A novel dry stick device construction for the determination of an analyte in a sample is provided. The device comprises: (i) optionally a solid support, (ii) at least one reagent pad comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device when in a non-moistened state, and (iii) a regulating pad being in contact with the at least one reagent pad, the regulating pad creating a second environment for said reagent(s), when in a moistened state, said second environment permitting an increased rate of reaction between the analyte and the reagent.

77 Claims, No Drawings

DRY STICK DEVICE CONSTRUCTION AND METHOD FOR DETERMINING AN ANALYTE IN A SAMPLE USING SAID DRY STICK DEVICE

CROSS-REFERENCE TO RELATED APPLICATIONS

The present Application is a U.S. national phase of PCT/DK/2007/05004 filed on Jan. 19, 2007 ("CPCT Application"), which claims priority from Denmark Application No. PA 2006 00084 filed on Jan. 19, 2006 and U.S. Provisional Application No. 60/759,953 filed on Jan. 19, 2006, all three of which are hereby incorporated by reference in their entirety into the present Application. The PCT Application, incorporated herein by reference includes any amendments in the PCT Application including Amendments Under PCT Article 19, any amendments associated with the International Search Report and the International Preliminary Report on Patentability, and amended claims received by the International Bureau on Apr. 2, 2008.

FIELD OF THE INVENTION

The present invention relates to the field of dry stick devices and their use in analysing an analyte in a sample. In particular the present invention relates to an improved dry stick device construction for the determination of an analyte in a sample, wherein particularly storage stability and performance of the dry stick device have been considered.

PRIOR ART

The demand for rapid and reliable diagnostical tests in clinical testing is increasing. Today significant parts of the diagnostic tests employed in clinical testing consist of test papers impregnated with several compounds, thus creating a non-differentiated reactive paper. When using such test papers the reactive paper is merely put into contact with the material in suspect (e.g. a body fluid) thereby creating a colour change or a change in colour intensity which is used to verify whether or not a particular effect is achieved or to quantitatively determine the amount of an analyte present in the sample.

Currently clinical laboratory methods used for diagnosis of the physiological and nutritional condition, such as the diagnoses of mastitis in an animal, is primarily based on SCC (somatic cell count) of e.g. milk and the differentiation of bacterial pathogens in milk samples.

Thus, conventionally used tests for the detection of inflammation caused by mastitis in an animal, have, until now, consisted of rather complex liquid systems whereby test tubes, measuring devices, ultraviolet light, standardization of instruments, correction factors depending upon temperature raise the prevalence of false readings.

Mastitis affects the integrity of mammary gland structure and concurrently damages the secretary epithelia and the blood-milk barriers. Consequently, many milk components are influenced by mastitis. Major components such as fat, protein and lactose are reduced and a number of enzymes are altered.

Different factors, other than SCC-determination, that may be used as suitable indicators for the inflammation caused by mastitis in an animal may be lactate dehydrogenase (LDH) and/or N-acetyl glucosaminidase. N-acetyl-β-D-glucosaminidase, also called N-acetyl glucosaminidase (NAGase), has been claimed to be one of the better markers for mammary inflammation. Furthermore, it has been shown that other enzymes in milk, like LDH may be of similar value as this enzyme as well as NAGase can be used as a suitable indicator of mastitis.

In the prior art a large number of methods for analysing analytes in fluid samples have been developed. These methods may be classified broadly into two kinds of systems, namely a reaction system in which the reaction is conducted in a solution (also called wet chemistry) and a reaction system in which the reaction is conducted in a solid phase carrier (also called dry chemistry).

The analytical reaction based on wet chemistry includes a large number of procedures, varying widely from an analytical procedure of the so called manual method in which no machine is used at all to use of automatic analytical instrument.

However, such wet chemistry is carried out basically in the form of an aqueous solution, and requires some handling steps which involve various problems. One problem that may appear relates to the enhanced amount of water present, whereby an increased consumption of energy may be caused. Furthermore, great skills for performing the assay may be required for the operations, thus necessitating enormous amounts of time and labour, and the waste liquors produced may cause environmental pollution and therefore requires further handling.

On the other hand, analytical methods utilizing dry chemistry for the analytical reactions have also been used widely, and these are generally practiced in the form of non-differentiated filter paper or other porous materials impregnated with one or more reagents capable of generating a detectable signal.

U.S. Pat. No. 3,867,259 (by Forgione) discloses a diagnostic test device (a dry stick) for determining the concentration of LDH in sera. The test device comprises a bibulous material which has contained therein the dried residue resulting from the impregnation of the bibulous material with (i) a tetrazolium salt (ii) a chromatographic effect preventor, (iii) an antioxidant, (iv) diaphorase and (v) a nicotinamide-adenine-dinucleotide.

Lippenheide et al. (1995) describes measuring LDH in milk using both wet and dry chemistry. Lippenheide et al. concluded that high precision, accuracy and easy handling are achieved by employing dry chemistry analysis relative to wet chemistry analysis, however Lippenheide et al. do not describe a specific construction of the dry stick device.

Despite the recommendations by Lippenheide et al. it is a fact, that the dry stick devices available on the market today and the dry stick devices described in prior art like U.S. Pat. No. 3,867,259 as mentioned above consists of a non-differentiated material impregnated with one or more reagent(s). Dry stick devices comprising non-differentiated environments compromise both the storage stability and the performance of the impregnated reagent(s) as optimal storage stability are hardly ever achieved at the same environmental conditions (e.g. pH and/or salt content) as optimal performance of the dry stick. Thus, by employing non-differentiated dry stick devices the environment of the material i.e. pad(s) has been created in such a way that the dry stick device displays acceptable (but not optimal) storage stability and acceptable (but not optimal) performance.

Therefore, it may be of interest to provide a dry stick device such as a differentiated dry stick, which simultaneously displays improved storage stability and improved performance during the assaying compared to conventional produced dry stick devices.

Consequently, there exists a need for an improved dry stick device such as a differentiated dry stick device wherein the storage stability and/or performance of the dry stick device have been significantly improved thus providing differentiated pad environments each optimised so as to significantly improve storage stability and performance of the reagent(s) and thus the dry stick device. This need has been satisfied by the present invention which is more fully discussed herein below.

SUMMARY OF THE PRESENT INVENTION

Accordingly, the aim of the present invention is in a first aspect to provide an improved dry stick device construction for the determination of an analyte in a sample. Preferably the improved dry stick device relates to a differentiated dry stick device for the determination of an analyte in a sample.

The dry stick device construction consists of at least one reagent pad comprising a reagent or a combination of reagents capable of reacting with the analyte, a derivative of said analyte or an indicator compound for said analyte in order to provide a detectable signal when in a moistened state. The at least one reagent pad provides a first environment for the reagent(s) thereby permitting an improved storage stability of the reagent(s) and of the dry stick device when in a non-moistened state. Moreover the dry stick device consists of a regulating pad, which is in contact with the at least one reagent pad. The regulating pad creates a second environment for the reagent(s) when in a moistened state, thereby allowing an increased rate of reaction between the analyte and the reagents when in a moistened state. When in use, the sample suspected of containing the analyte is applied to the at least one reagent pad of the dry stick device. The sample migrates into the at least one reagent pad and solubilise the reagent(s) and thus alone or together with the reagent(s) migrate from the at least one reagent pad into the regulating pad which is in contact with the at least one reagent pad. The regulating pad creates when in a moistened state a second environment, permitting an increased rate of reaction between the analyte and the reagents hence allowing the reagent and the analyte, the derivative of said analyte or the detectable compound of said analyte to provide a detectable signal which directly or indirectly is capable of being observed either by a suitable instrument, apparatus or by visual inspection In an aspect of the present invention, the device comprises:
 (i) optionally a solid support,
 (ii) at least one reagent pad comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device when in a non-moistened state
 (iii) a regulating pad being in contact with the at least one reagent pad, the regulating pad creating a second environment for said reagent(s) when in a moistened state, said second environment permitting an increased rate of reaction between the analyte and the reagent(s).

In another aspect of the present invention a method is provided for assaying an analyte in a sample. The method comprises the steps of:
 (i) applying the sample suspected of containing the analyte to a reagent pad
 (ii) permitting the sample to migrate into the reagent pad comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device when in a non-moistened state
 (iii) permitting the sample, alone or together with the reagent, to migrate from the reagent pad into a regulating pad, said regulating pad being in contact with the reagent pad, the regulating pad creating a second environment for said reagent when in a moistened state, said second environment permitting an increased rate of reaction between the analyte and the reagent, and
 (iv) permitting the reagent and the analyte, the derivative of said analyte or the indicator compound for said analyte to provide a detectable signal.

In yet an aspect of the present invention a method Is provided for the preparation of the dry stick device according to the present invention. The method comprises the steps of:
 (i) providing a reagent pad by impregnating a first porous material with an aqueous solution comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device
 (ii) thereafter drying the reagent pad,
 (iii) providing a regulating pad by impregnating a second porous material with an aqueous solution creating a second environment for said reagent(s) when in a moistened state, said second environment permitting an increased rate of reaction between the analyte and the reagent,
 (iv) thereafter drying the impregnated second porous material, and
 (v) contacting the reagent pad with the regulating pad, optionally on a solid support, to obtain the dry stick device.

In a further aspect of the present invention a method is provided for assaying lactate dehydrogenase (LDH) in a sample. The method comprises the steps of:
 (i) applying the sample suspected of containing LDH to the reagent pad
 (ii) permitting the sample to migrate into the reagent pad comprising a reagent or a combination of reagents capable of reacting with LDH, a derivative of LDH or an indicator compound for LDH to provide a detectable signal when in a moistened state, the at least one reagent pad providing a first environment for said reagent(s), said first environment permitting an improved storage stability of the reagent(s) and dry stick device when in a non-moistened state.
 (iii) permitting the sample to migrate from the reagent pad into a regulating pad, said regulating pad being in contact with the reagent pad, the regulating pad creating a second environment for said reagent, when in a moistened state, said second environment permitting an increased rate of reaction between LDH and the reagent(s), and
 (iv) permitting the reagent and LDH, the derivative of LDH or the indicator compound for LDH to provide a detectable signal.

Additional aspects of the present invention relate to methods similar to the method mentioned above for assaying LDH in a sample wherein the assayed compound is e.g. urea, beta-hydroxybutyrate (BNB), N-acetyl glucosaminidase (NA-Gase), glucose or lactose.

In a last aspect of the present invention, a method is provided for laminating two or more pads. The method comprising the steps of:
(i) providing a least a first pad and a second pad
(ii) applying an adhesive to one side of the first pad, said adhesive comprises water/liquid permeable regions
(iii) contacting said second pad with the adhesive attached to the first pad, thereby creating two layers The present invention will be described in more detail in the following.

DETAILED DISCLOSURE OF THE PRESENT INVENTION

The inventors of the present invention surprisingly discovered and developed a new dry stick device construction that simultaneously comply with the requirements of good stability during storage and good performance during testing or assaying. This dry stick device may have the construction of a differentiated dry stick device.

In the present context the term "differentiated" relates to a dry stick device having different environments (such as different pH-values and/or salt concentration) in the same dry stick. These different environments participate in improving the storage stability of the impregnated reagents and the dry stick as well as improving the reaction rate of the dry stick when assaying the analyte. The term "non-differentiated" relates on the other hand to a dry stick device conprising only one environment in which the impregnated reagent(s) are stored.

The construction of the new dry stick device for the determination of an analyte in a sample comprises: (i) optionally a solid support, (ii) at least one reagent pad comprising a reagent or a combination of reagents capable of reacting with the analyte, a derivative of said analyte or an indicator compound for said analyte to provide a detectable signal when in a moistened state, the at least one reagent pad providing a first environment for said reagent(s) said first environment permitting an improved storage stability of the reagent(s) and dry stick device when in a non-moistened state, and (iii) a regulating pad being in contact with the at least one reagent pad, the regulating pad creating a second environment for said reagent(s) when in a moistened state, said second environment permitting an increased rate of reaction between the analyte and the reagent(s).

It may be preferred that the method and the device of the present invention for the determination of the analyte is based on an enzyme-based determination. The activity of enzymes is strongly affected e.g. by changes in pH or by a change in salt concentration of the surrounding environment. In respect of the pH-dependency it is generally known that each enzyme works best at a certain pH (the pH-optimum of the enzyme) and that its activity decreases at values above and below that point, but to some extent there will be an activity of the enzyme at pH-values deviating from this pH-optimum. Additionally, it is known for the person skilled in the art that this pH-optimum is different from one enzyme to another and the range between the different optimal pH-values may be large. For instance/ the normal pH-optimum for most of the human enzymes is between pH 6 and 8, however, the protein-digesting enzyme pepsin secreted in the stomach is only active in an acidic medium and has a pH-optimum at pH 2, whereas the optimal pH-value for trypsin, an enzyme splitting proteins secreted from the pancreas has a pH-optimum at pH 8.5.

Therefore, it may be of interest during the assaying to provide a pH-value which is as close to the pH-optimum of the enzyme of the assay as possible to obtain a fast reaction. Furthermore, other factors such as salt concentration may influence enzyme activity. Here again it may be advantageous to provide a salt concentration as close to the optimal salt concentration for the enzyme as possible in order to obtain a fast reaction.

In the present invention the term "first environment" relates to a condition around the reagent or the combination of reagents in the reagent pad when in non-moistened state in which the reactivity of the reagent or combination of reagents is decreased from the reactivity under optimal conditions (also when in non-moistened state). It is obvious that these conditions are different depending on the enzyme being present and/or the enzyme being determined as the analyte. The optimum conditions are known to the skilled person and may be found in the prior art. In a preferred embodiment of the present invention the condition in the first environment may be provided by removing an activator, by regulating the pH-value to a value different from the optimal pH-value of the enzyme(s), e.g. by the removal of an acid or a base, or by combining the addition of an activator with the regulation of the pH-value. In an embodiment of the present invention the activator may be a salt.

In a preferred embodiment of the present invention the condition in the first environment may be selected to favour the storage stability of the reagent(s) capable of reacting with the analyte for providing a detectable signal.

The storage time for the dry stick device according to the present invention may be substantially extended due to the new construction of the dry stick device. Extended storage time, as provided by the present invention, relates to longer storage time without significant loss of performance during assaying. Thus, the storage time of the dry stick device according to the present invention may be at least 15% longer than a similar conventional developed dry stick device, such as 20% longer, such as 50% longer, e.g. 75% longer, such as 100% longer, e.g. 150% longer, such as 200% longer, e.g. 300% longer or such as 500% longer.

In an embodiment of the present invention the condition in the first environment is provided by adjusting the pH-value to a value that deviates from the optimal pH-value of the enzyme(s). Preferably, the deviation from the optimum may be at least 0.5 pH-units, such as at least 0.75 pH-units, e.g. at least 1 pH-units, such as at least 1.25 pH-units, e.g. at least 1.5 pH-units, such as at least 1.75 pH-units, e.g. at least 2 pH-units, such as at least 2.5 pH-units, e.g. at least 3 pH-units, such as at least 3.5 pH-units, e.g. at least 4 pH-units, such as at least 4.5 pH-units or e.g. at least 5 pH-units.

In the present invention the term "second environment" relates to a condition in the dry stick device around the reagent or the combination of reagents provided by the regulating pad when in moistened state in which the reactivity of the reagent or combination of reagents (initially impregnated in the at least one reagent pad) approaches optimal conditions of the enzyme(s) in order to improve reactivity of the enzymes. This means that the regulating pad is provided to introduce a change in the dry stick device that brings the reagents and/or the analyte from a substantially inactive state or from a state of reduced activity to a state of increased activity capable of providing a reliable, reproducible and easy determination of the analyte.

Again, it is obvious that the optimal conditions are different depending on the enzyme being present and/or the enzyme being determined as the analyte, and that the optimum conditions are known for the skilled person and may be found in the prior art. In a preferred embodiment of the present invention the condition in the second environment may be provided by addition of an activator, by regulating the pH-value to a value close to the optimal pH-value of the enzyme(s), e.g. by the addition of an acid or a base, or by combining the addition of an activator with the regulation of the pH-value.

In a preferred embodiment of the present invention the condition in the second environment is selected in such a manner as to favour the reactivity performance of the reagent(s) capable of reacting with the analyte and providing a detectable signal or in such a manner as to favour the rate of reaction between the analyte and the reagent(s) capable of reacting with the analyte providing a detectable signal.

In another embodiment of the present invention the condition in the second environment is provided by regulating the pH-value to a value that approaches the optimal pH-value of the enzyme(s). Preferably, the pH-value deviates from the optimum pH-value by less than 2 pH-units, such as less than 1 pH-unit, e.g. less than 0.75 pH-units, such as less than 0.5 pH-unit, e.g. less than 0.25 pH-units, such as less than 0.1 pH-unit or e.g. less than 0.05 pH-units.

When the assay involves two or more enzymes having different optima the second environment may deviate from the optimal condition in order to consider all the enzymes participating in the assay to favour the assay of the analyte. In an embodiment of the present invention the deviation from the optimum may be less than 2 pH-units, such as less than 1 pH-unit, e.g. less than 0.75 pH-units, such as less than 0.5 pH-unit, e.g. less than 0.25 pH-units, such as less than 0.1 pH-unit or e.g. less than 0.05 pH-units.

In a preferred embodiment of the present invention the method and the device provided involve an enzyme-based determination of an analyte. This includes the types of assays where one or more enzymes is/are impregnated into the at least one reagent pad and the analyte may or may not be an enzyme. However, enzyme-based determination of an analyte also relates to assays where the analyte to be determined is an enzyme irrespective of the presence of an enzyme being impregnated in the reagent pad or not. It is preferred that the assay is one where an enzyme is impregnated in the at least one reagent pad and the analyte may or may not be an enzyme.

The inventors of the present invention have also provided a new method for assaying an analyte in a sample. The method comprises the steps of:
(i) applying the sample suspected of containing the analyte to a reagent pad
(ii) permitting the sample to migrate into the reagent pad comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device
(iii) permitting the sample, alone or together with the reagent, to migrate from the reagent pad into a regulating pad, said regulating pad being in contact with the reagent pad, the regulating pad creating a second environment for said reagent when in a moistened state, said second environment permitting an increased rate of reaction between the analyte and the reagent, and
(iv) permitting the reagent and the analyte, the derivative of said analyte or the indicator compound for said analyte to provide a detectable signal.

The detectable signal may be any substance which directly or indirectly is capable of being observed by any kind of visual or instrumental means. The instrumental means may be e.g. a magnetometer, a spectrophotometer, or an ELISA-reader. Various suitable compounds may be suitable as the colour producing compound. In the present invention the colour producing compound may be selected from the group consisting of chromogens, catalysts, fluorescent compounds, chemiluminescent compounds, radioactive labels, metals, magnetic particles, dye particles, enzymes or substrates, or organic polymer latex particles; liposomes or other vesicles containing signal producing substances and the like.

The sample to be assayed may be applied to the dry stick device either by applying the sample or a subset of the sample to the dry stick device or by putting the dry stick device into a container comprising the sample. In step (i) it is suggested to apply the sample suspected of containing the analyte, or a subset thereof to the reagent pad.

In another embodiment of the present invention the sample is applied to the reagent pad and the method for assaying an analyte in a sample may comprise the steps of:
(i) applying the sample suspected of containing the analyte to a reagent pad
(ii) permitting the sample to migrate into the reagent pad comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device
(iii) permitting the sample, alone or together with the reagent, to migrate from the reagent pad into a regulating pad, said regulating pad being in contact with the reagent pad, the regulating pad creating a second environment for said reagent when in a moistened state, said second environment permitting an increased rate of reaction between the analyte and the reagent, and
(iv) permitting the reagent and the analyte, the derivative of said analyte or the indicator compound for said analyte to provide a detectable signal.

Alternatively the sample suspected of containing the analyte, or a subset thereof may be applied to a separate application pad which is capable of receiving and distributing the sample (preferably substantially homogeneously) into the reagent pad and the regulation pad, respectively.

In the present context the term "application pad" relates to a pad in the device where the liquid sample is applied to the device and which provides a fast adsorption of the liquid sample and a fast and consistent release of a sample to the reagent pad and/or to the regulating pad. Accordingly, the material used in the application pad may be selected from the group consisting of a nitrocellulose membrane, a cellulose, a polymer such as nylon, a polyvinylidene fluoride or latex, glass fibres, woven fibres, non-woven fibres and a chromatographic gel membrane. Preferably, the material used in the first environment is a woven or a non-woven glass fibre.

When a sample is applied to the application pad it migrates into the reagent pad and/or regulating pad (steps (ii) and (iii) in the respective build-ups) thus transforming the first and second environment into moistened states. In the present context the term "in a moistened state" relates to the contact between reagent(s) in the reagent(s) pad and/or the agent in the regulating pad and the sample whereby the reagent(s) pad and/or the regulating pad becomes wet or slightly wet. The effect of the moistened state is that the dried reagents, the dried chemicals and/or dried components are liberated and dissolved (mobilised) and the reaction in the dry stick device commences and a detectable signal is produced, dependent on the amount of analyte present in the sample. In an embodiment of the present invention the application pad forms part of the reagent pad and/or the regulation pad.

The Porous Material

The materials selected to be used in the at least one reagent pad and/or the regulating pad may be selected from a porous material. In the present context the term "porous material" relates to a material which adsorbs the sample and thereby permits it to migrate. The porous material selected may comprise a pore-size which has a capacity that makes it possible to provide a high flow-rate which quickly dissolve the reagent or the combination of reagents and which provides a good and substantially even distribution of the samples. Preferably, the porous material may be selected for providing substantially no retention of triglyceride rich samples. In an embodiment of the present invention the retention of triglycerides is 0%, such as at the most 1%, e.g. at the most 2.5%, such as at the most 5%, e.g. at the most 10%, such as at the most 15%, in the, e.g. at the most 25%, such as at the most 50%, or the retention of most or all of the triglycerides, e.g. at the most 75%, such as at the most 100%.

The porous material is preferably selected from the group consisting of a nitrocellulose membrane, a cellulose, a polymer, such as nylon, a polyvinylidene fluoride or latex, glass fibres, woven fibres, non-woven fibres, a chromatographic gel membranes, diatomaceous earth, silica gel, silicium oxide and kieselguhr.

In an embodiment of the present invention, the porous material in the at least one reagent pad and/or the regulating pad may be selected from a group of materials comprising a pore size preferably in the range of 10-30,000 µm, such as in the range of 10-20,000 µm, for instance in the range of 10-10, 000 µm, for instance in the range of 10-1000 µm, such as in the range of 10-500 µm, such as in the range of 10-100 µm, for instance in the range of 10-75 µm, such as in the range of 10-50 µm, for instance in the range of 50-200 µm, such as the range of 50-100 µm, for instance in the range of 100-500 µm, such as the range of 50-300 µm, for instance in the range of 75-300 µm, such as the range of 75-200 µm, for instance in the range of 75-150 µm, such as the range of 75-120 µm.

In yet an embodiment of the present invention, the porous material in the at least one reagent pad and/or the regulating pad may be selected from; a group of materials comprising a suitable pore size such as at most 500 µm, for instance at most 200 µm, such as at most 150 µm, for instance at most 100 µm, such as at most 75 µm.

In another embodiment of the present invention, the porous material in the at least one reagent pad and/or the regulating pad may be characterised by having a high capacity of binding proteins such as in the range of 1-400 µg/cm$^2$, for instance the range of 1-250 µg/cm$^2$, such as the range of 1-200 µg/cm$^2$, for instance the range of 1-140 µg/cm$^2$, such as the range of 1-120 µg/cm$^2$, for instance the range of 1-100 µg/cm$^2$, such as the range of 1-80 µg/cm$^2$, for instance the range of 1-60 µg/cm$^2$, such as the range of 1-40 µg/cm$^2$, for instance the range of 50-200 µg/cm$^2$, such as the range of 50-100 µg/cm$^2$, for instance the range of 50-150 µg/cm$^2$, such as the range of 50-120 µg/cm$^2$, for instance the range of 75-120 µg/cm$^2$, such as the range of 75-110 µg/cm$^2$.

In a further embodiment of the present invention, the porous material in the at least one reagent pad and/or the regulating pad may be characterised by having a high capacity of binding proteins such as at most 400 µg/cm$^2$, for instance at most 250 µg/cm$^2$, such as at most 200 µg/cm$^2$, for instance at most 140 µg/cm$^2$, such as at most 120 µg/cm$^2$, for instance at most 100 µg/cm$^2$, such as at most 80 µg/cm$^2$, for instance at most 60 µg/cm$^2$, such as at most 40 µg/cm$^2$.

Accordingly, in an embodiment of the present invention, the porous material in the at least one reagent pad and/or the regulating pad may be characterised by permitting the sample to migrate with a high capillary flow rate, such as in the range of 50-500 sec/4 cm, for instance the range of 50-250 sec/4 cm, such as the range of 50-200 sec/4 cm, such as the range of 50-100 sec/4 cm, for instance the range of 50-75 sec/4 cm, such as the range of 100-250 sec/4 cm, for instance the range of 150-250 sec/4cm, such as the range of 200-250 sec/4 cm and for instance the range of 250-500 sec/4 cm, such as the range of 75-150 sec/4 cm and for instance the range of 80-130 sec/4 cm, such as the range of 80-110.

In another embodiment of the present invention, the porous material of the at least one reagent pad and/or the regulating pad may be characterised by permitting the sample to migrate with a high capillary flow rate, such as at most 300 sec/4 cm, for instance at most 200 sec/4 cm, such as at most 100 sec/4 cm, such as at most 75 sec/4 cm.

Preferably, the porous materials used in the at least one reagent pad and/or the regulating pad may be the same in at least 2 of the pads, such as at least 3 of the pads, for instance 4 of the pads, such as at least 5 of the pads.

In accordance with the above porous material, it may be desirable to provide a device for detecting an analyte in a fast assay. In an embodiment of the present invention the assay time is less than 15 minutes, such as less than 10 minutes, e.g. less than 8 minutes, such as less than 7 minutes, e.g. less than 6 minutes, such as less than 5 minutes, e.g. less than 4 minutes, such as less than 3 minutes, e.g. less than 2 minutes, such as less than 1 minute, e.g. less than 30 seconds.

The Reagent Pad

In the present context the term "reagent pad" relates to one or more pads comprising a reagent or a combination of reagents. The reagent or the combination of reagents may preferably be impregnated into the reagent pad in such a manner that the reagent or the combination of reagents is/are immobilised when in dry state and mobile when in moistened state.

In the present context of the present invention the term "reagent" relates to the chemical substance or an enzyme that reacts with or participates in or is necessary for the determination of an analyte, a derivative of said analyte or an indicator compound for said analyte to provide a detectable signal. Similar definition of the combination of reagents may be provided which relates more specifically to 2 or more reagents, such as 3 or more reagents, e.g. 4 or more reagents, such as 5 or more reagents, e.g. 6 or more reagents.

In an embodiment of the present invention the dry stick test device comprises at least 2 reagent pads, such as at least 3 reagent pads, e.g. at least 4 reagent pads, such as at least 5 reagent pads, e.g. at least 6 reagent pads. In this embodiment the reagents that react with or participate in or are necessary for the determination of an analyte, a derivative of said analyte or an indicator compound for said analyte to provide a detectable signal may be introduced into different reagent pads. This may improve stability, storage properties and applicability of the dry stick device because non-compatible compounds can be included in different reagent pads and hence different environments of the dry stick device.

The Regulating Pad

In the present context the term "regulating pad" relates to a pad capable of regulating the environment of the sample comprising the analyte to a second environment for the sample in order to facilitate determination of the analyte, a derivative of said analyte or an indicator compound for said analyte.

In an embodiment of the present invention the regulating pad may comprise one or more agents capable of increasing the rate of the reaction. Such agents may add an effect by providing an activator, by providing a change in pH by the addition of an acid, a base or by a combination thereof.

In yet an embodiment of the present invention the regulating pad is in contact with at least one reagent pad by substantially fully overlapping, by partially overlapping or by laying adjacent to the at least one reagent pad. In an embodiment of the present invention the regulating pad is overlapping the at least one reagent pad by at least 5%, such as at least 10%, e.g. at least 25%, such as at least 50%, e.g. at least 75%, such as at least 80%, e.g. at least 90%, such as at least 95%. In the present context the term "substantially fully overlapping" relates to two separate pads (the regulating pad and the at least one reagent pad) being placed on top of one another. In the present context the term "partially overlapping" relates to two separate pads (the regulating pad and the at least one reagent pad) being overlapping with only part of the pad(s). A partial overlap of 100% relates to a full overlap and a deviation of 5% from the 100% full overlap relates to a substantially full overlap.

In an embodiment of the present invention the regulation pad and the at least one reagent pad(s) are laying adjacent to one another. This means that the pads are placed in contact with each other (touching each other). An overlap of 0% (but in contact) relates to the term "laying adjacent", furthermore, an overlap of less than 5% may be considered being within the term of "laying adjacent", such as an overlap of at the most 4%, e.g. an overlap of the most 3%, such as an overlap of the most 2% or e.g. an overlap of the most 1%.

In yet an embodiment of the present invention the regulation pad and the at least one reagent pad may be combined in one pad where the reagent(s) and the agent(s) capable of increasing the rate of the reaction may be impregnated individually and may optionally be separated by a coating. A system, a method and various chemicals useful for preparing a pad comprising all the substances (reagent(s) and agent(s) capable of increasing the rate of the reaction) into one pad have been described in U.S. Pat. No. 4,215,995 which is hereby incorporated by reference.

In an embodiment of the present invention one or more reagents may be incorporated into the regulation pad, whereas the reagent(s) sensitive to the second environment, to the chemical composition or to the reagents of the assay may be removed into a separated pad e.g. the reagent pad.

The Solid Support

The device according to the present invention, may be supported by a solid support. In the present context, the term "solid support" refers to a material, which has no influence on the migration or on the reaction of the liquid sample or on reagent(s) or the agents capable of increasing the rate of the reaction. The solid support provides a stabilising basis for the assay device and provides sufficient strength to maintain the desired physical shape and has substantially no interference with the production of a detectable signal.

In an embodiment of the present invention, the material for the solid support is selected from the group consisting of tubes, polymeric beads, nitrocellulose strips, membranes, filters, plastic sheets and the like.

Naturally, synthetic and natural occurring materials that are synthetically modified can be used as the material of the solid phase. Such materials include polysaccharides, for instance cellulosic materials such as paper and cellulosic derivatives, such as cellulose acetate and nitrocellulose, silica, inorganic materials, such as, for example, deactivated alumina, diatomaceous earth, $MgSO_4$ or other inorganic finely divided material uniformly dispersed in a porous polymeric matrix, wherein the matrix may comprise one or more polymers such as homopolymers and copolymers of vinyl chloride, for instance, polyvinyl chloride, vinyl chloride-propylene copolymer, and vinyl chloride-vinyl acetate copolymer, cloth, both naturally occurring (for instance, cotton) and synthetic (for instance, nylon), porous gels, such as silica gel, agarose, dextran, and gelatin, polymeric films, such as polyacrylamide, and the like.

In an embodiment of the present invention the solid support may be omitted from the dry stick device. In this case the dry stick device comprises at least one reagent pad and a regulating pad. When performing a determination of an analyte in a sample using a dry stick device without a solid support the sample may by applied to the dry stick device of one surface and the detectable signal may be detected on the same or another surface of the device.

The Analytes to be Determined

A device or a method based on the above principles can be used to determine a wide range of analytes by choice of appropriate colouring compounds known to the person skilled in the art, and the invention need not to be limited to examples mentioned herein.

In an embodiment of the present invention the analytes to be assayed can be selected from the group consisting of a protein, an enzyme, a fat, a carbohydrate, an antibiotic, a steroid, such as hormones, a vitamin, a chemical compound, a hapten, a cell, such as a bacteria or such as leukocytes, an antibody, a drug of abuse and blood.

In an embodiment of the present invention the analyte is an enzyme and the enzyme is preferably selected from the group consisting of catalase, lactate dehydrogenase (LDH), alkaline phosphatase, acid phosphatase, carboxylesterase, arylesterase, β-glucuronidase, lactoperoxidase, lipase, lysozyme, xanthine oxidase, plasmin and beta-N-acetylhexosa-minidase (NAGase), prostaglandin D synthase (PGDS).

In yet an embodiment of the present invention the analyte is a chemical compound and the chemical compound may be selected from the group consisting of urea, triglyceride and ketone bodies, such as acetoacetate, beta-hydroxybutyrate (BOHB), acetone, ascorbic acid, nitrates, urobilinogen, cholesterol, and steroids such as pregnenolone, progesterone, testosterone, dihydrotestosterone, estrone, estradiol, cortisol, cortisone, aldosterone, corticosterone, androstenedione, 17α-OH-pregnenolone, 17α-OH-progesterone, 11-desoxycorticosterone, 11-desoxycortisol and dehydroepiandrosterone, luteinising hormone or human chorionic gonadotropin.

In a further embodiment of the present invention the analyte is a carbohydrate and the carbohydrate may be selected from the group consisting of a monosaccharide, such as glucose or galactose, and a disaccharide, such as lactose.

The Samples to be Analysed

In the present context the term "a sample" relates to any sample found in the form of liquid, solid or gas and which may be liquefied at the time of assaying. In order to wet the porous material used in the regulation pad and/or in the at least one reagent pad to permit migration, a liquid sample may be applied. Furthermore, it is preferred that a minimum number of handling steps of the liquid sample is necessary before applying it to the dry stick test device. In the present context, the term "handling steps" relates to any kind of pre-treatment of the liquid sample before or after it has been applied to the assay device. This pre-treatment comprises separation, filtration, dilution, distillation, concentration, inactivation of interfering compounds, centrifugation, heating, fixation, addition of reagents, or chemical treatment.

In an embodiment of the present invention the sample may be collected from a mammal, preferably the mammal is selected from the group consisting of herd animals, cows, camels, buffaloes, pigs, horses, deer, sheep, goats, pets, dogs, cats and humans.

In a preferred embodiment of the present invention, the sample can be derived from any desirable source, however, it is preferred that the sample is selected from the group consisting of milk, blood, serum, plasma, saliva, urine, sweat, ocular lens fluid, cerebral spinal fluid, ascites fluid, mucous fluid, synovial fluid, peritoneal fluid, amniotic fluid or the like.

Besides physiological fluids, other liquid samples such as various water samples, food products, waste water and the like can be used. In addition, a solid test sample can be used once it is modified to form a liquid sample, for instance in the form of a solution, a suspension or an emulsion.

The Colouring Compound

In the present context the term "colouring compound" relates to a chemical compound capable of developing and emitting a detectable signal, such as producing a colour. The intensity of this colour varies in intensity depending upon the concentration of the analyte present in the sample.

Examples of colouring compounds suitable in each specific assay may be easily recognised by the person skilled in the art and these colouring compounds may be introduced into a dry stick test device according to the present invention.

In an embodiment of the present invention the colouring compound is selected from the group consisting of a tetrazolium salt; 4-aminoantipyrine/3,5-dimethoxy-N-ethyl-N-(2-hydroxy-3-sulfopropyl)-aniline sodium salt; 4-aminoantipyrine/1-naphthol-3,6-disulfonic acid-2-sodium salt; 4-aminoantipyrine/N-ethyl-N-(2-hydroxy-3-sulfopropyl)-m-toluidine sodium salt; 4-aminoantipyrine/1,7-dihydroxynaphthalene; 4-aminoantipyrine/3,5-dichloro-2-hydroxybenzene sulfonate; Tetrazolium violet; 3,5-dinitrobenzoic acid; Copper sulfate; N-1-naphthyl-N'-diethylenediamine-oxalic acid; Fast Red TR salt; Bromocresol green; Bromophenol blue; Arsenazo III; 2-(3,5-dimethoxy-4-hydroxyphenol)-4,5-bis(4-dimethylaminophenyl)-imidazole; Pyridylazo dye; Magenta coupler dye; 1,5-bis(2-hydroxy-3,5-dichlorophenyl)-3-cyano formazan; Copper tartrate; 3-methyl-2-benzothiazolinone hydrazone; N-propyl-4-(2,6-dinitro-4-chlorobenzyl)quinolinium ethane sulfonate; Hydroxydiaryl imidazole; 2-methoxy-4-morpholinophenyl diazonium tetrachlorozincate; 3,3',5,5'-tetramethylbenzidine; 4-aminophenazone/3,5-dichloro-2-hydroxybenzene sulfonate; Primaquine diphosphate/3-methyl-2-benzothiazoline hydrazone; 2,5-dinitrobenzoic acid; 2-(p-indophenyl)-3-(p-nitrophenyl)-5-phenyltetrazolium chloride; 3-hydroxy-1,2,3,4-tetrahydrobenzo-(h)-quinoline; or any derivative thereof.

Increasing Rate of Reaction

As mentioned above the regulating pad provides a second environment for said reagent(s), when in a moistened state, permitting an increased rate of reaction between the analyte and the reagent In an embodiment of the present invention the increased rate of reaction is provided by an activator, a change in pH by the addition of an acid, a base or a combination thereof.

In the present context the term "activator" relates to a substance, other than the analyte or one of the reagents, that increases the rate of a reaction, such as a catalysed reaction, without itself being consumed, the process may be called activation. An activator of an enzyme-catalysed reaction may be called enzyme activator and it may act by binding (directly or indirectly) to the enzyme.

The choice of activator(s) and the combination of activators is dependent on the type of analyte to be assayed and the assay to be used. This depends on what kind of activator(s) may easily be recognised by the person skilled in the art and may be found in the litterature (e.g. in the book: by Trevor Palmer, 2. edition, "Understanding Enzymes" published in 1985). Preferably, the activator is a metal ion, such as a mono-, di- or trivalent metal ion.

In an embodiment of the present invention the mono-, di-or trivalent metal ion (cation) may be selected from the group consisting of $Na^+$, $K^+$, $Ca^+$, $Mg^{2+}$, $Cu^{2+}$, $Fe^{2+}$, $Fe^{3+}$, $Zn^{2+}$, $Mn^{2+}$ and any combination thereof.

In another embodiment of the present invention the activator may be an anion. Preferably, the anion may be selected from the group consisting of acetates, sulfates, carbonates, chlorides and nitrates The Ancillary Compound Because of the complexity of the liquid samples to be assayed in the present invention it may occasionally be an advantage to use an ancillary compound in order to improve the flow and adsorption of the liquid sample in the regulation pad and/or in the one or more reagent pad(s) and to provide a fast, consistent and even release of the reagent(s) and the agents capable of increasing the rate of reaction. The ancillary compound may be supplied to the device either by a) adding it to the reagent pad(s) and/or regulation pad alone or together with the liquid sample, b) incorporating the ancillary compound into at least one of the reagent pad(s) and/or the regulation pad, or c) a combination thereof.

In an embodiment of the present invention, the ancillary compound is added to the dry stick device before the liquid sample is added. Preferably the ancillary compound is a liquid.

In another preferred embodiment of the present invention, the ancillary compound and the liquid sample are added to the dry stick device in layers. In the present context, the term "layers" refers to the splitting up of the volume of the ancillary compound and the volume of the liquid sample, and then the ancillary compound and the liquid sample are added to the first environment one after another. In this case, the ancillary compound may be added as a liquid as well as a solid compound. In an embodiment of the present invention, the ancillary compound and the liquid sample is split into at least 2 volumes each providing 4 alternating layers of ancillary compound and liquid sample, e.g. the ancillary compound and the liquid sample are split into at least 3 volumes each providing 6 alternating layers of ancillary compound and liquid sample, such as the ancillary compound and the liquid sample are split into at least 4 volumes each providing 8 alternating layers of ancillary compound and liquid sample, e.g. the ancillary compound and the liquid sample are split into at least 6 volumes each providing 12 alternating layers of ancillary compound and liquid sample, such as the ancillary compound and the liquid sample are split into at least 8 volumes each providing 16 alternating layers of ancillary compound and liquid sample, e.g. the ancillary compound and the liquid sample are split into at least 10 volumes each providing 20 alternating layers of ancillary compound and liquid sample, such as the ancillary compound and the liquid sample are split into at least 20 volumes each providing 40 alternating layers of ancillary compound and liquid sample.

In yet an embodiment of the present invention the ancillary compound may be impregnated into at least one reagent pad(s) and/or into the regulation pad.

In another embodiment of the present invention at least one reagent pad and/or the regulating pad incorporating at least one ancillary compound capable of improving the flow of the liquid sample.

In yet an embodiment of the present invention the ancillary compound provides a fast, consistent and homogenous release of the reagent(s) in the at least one reagent pad and/or the agent capable of increasing the rate of reaction in the regulating pad. Additionally, the ancillary compound provides low affinity for protein binding.

Furthermore, the ancillary compound may provide low retention of triglyceride rich samples and/or may decrease the viscosity of the sample.

In an embodiment of the present invention the ancillary compound contains chemical constituents selected from the group consisting of water, a surfactant, a salt, a metal, a sugar, a protein and a lipid.

Preparation of the Dry Stick

The dry stick device according to the present invention may be prepared by any conventional method provided for the preparation of dry stick devices. In a preferred embodiment the method for providing a dry stick device according to the present invention comprises the steps of:
 (i) providing a reagent pad by impregnating a first porous material with an aqueous solution comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device
 (ii) thereafter drying the reagent pad,
 (iii) providing a regulating pad by impregnating a second porous material with an aqueous solution comprising a second environment for said reagent(s) when in a moistened state, said second environment permitting an increased rate of reaction between the analyte and the reagent,
 (iv) thereafter drying the impregnated second porous material, and
 (v) contacting the reagent pad with the regulating pad, optionally on a solid support, to obtain the dry stick device.

The at least one reagent pad and the regulating pad may be contacted by substantially fully overlapping the pads, by partially overlapping of the pads or by laying the regulating pad adjacent to at least one reagent pad. In an embodiment of the present invention the arrangement of the pads may be selected in such a manner as to avoid precipitation of a sample component on the top face of the device. The sample components that may precipitate may be selected from the group consisting of proteins, carbohydrate, fat, cells, or other component present in the sample.

In a preferred embodiment of the present invention the first environment may be created in such a manner as to favour the storage of the reagent(s) capable of reacting with the analyte and providing a detectable signal—as described earlier. Furthermore, the second environment may be created in such a manner as to favour the performance of the reagent(s) capable of reacting with the analyte and providing a detectable signal—also as described earlier. Alternatively or additionally the second environment may be created in such a manner as to favour the rate of reaction between the analyte and the reagent(s) capable of reacting with the analyte providing a detectable signal—as described earlier.

In yet an embodiment of the present invention, the first environment may be created in such a manner as to favour the composition of the sample suspected of containing an analyte. In the case where the analyte may be found in milk, care should be taken if either the regulation pad or-the at least one reagent pad comprises a pH-value about 6 or less. If such a pad, having a pH-value about 6 or less, is placed on top of the other pads and is attached to the application pad to, the milk proteins may coagulate and form a precipitate on the top face of the dry stick device. This precipitate may cause a decrease in the intensity of the detectable signal. Thus, it may be preferred that such pad is being located down stream from the application pad in order to avoid decrease in the detectable signal.

Lamination Method

In an aspect of the present invention the two or more pads may be held together as described in prior art by use of a frame. Employing a frame will however take up space, be time exacting when the pads are to be placed herein and thus expensive. Accordingly it was the aim of the inventors of the present invention to create a fast, yet reliable, cost-efficient and relatively small dry stick.

In an embodiment of the present invention two or more pads may be subjected to at least one lamination method.

The method of laminating two or more pads may comprise the steps of:
 (i) providing a least a first pad and a second pad
 (ii) applying a film of an adhesive to one side of the first pad, said film of adhesive is obtained either by spraying
 (iii) creating film of adhesive permeable to liquid
 (iv) optionally placing the second pad on a flat surface, and
 (v) contacting said second pad with the first pad, thereby creating two layers
 (vi) laminating the two layers by applying pressure The method employed to laminate the at least two pads may be selected from the group consisting gluing, sewing, pressing or any combination hereof, preferably said glue may be selected from the group consisting of spray glue, aerosol glue and tape.

In the present context the term "laminating" relates to at least two pads, said pads are placed one over another or at least partly one over another. In the present context the term "first pad" relates to the at least one reagent pad and the term "second pad" relates to the regulation pad.

In a preferred embodiment of the present invention the adhesive may be applied in such a manner as to provide some permeability of the applied sample through the pads. The permeability must allow sufficient amounts of the applied sample to migrate through the two or more pads in order to ensure an at least partly mixture of the reagent(s) (reagent(s) present in the at least two environments, preferable within 1 minutes, such as within 2 minutes, e.g. within 3 minutes, such as within 5 minutes, e.g. within 5 minutes such as within 6 minutes, e.g. within 7 minutes, such as within 8 minutes, e.g. within 9 minutes, such as within 10 minutes.

In yet an embodiment of the present invention the at least two pads are after contacting the second pad with the adhesive attached to the first pad laminated by applying pressure. The pressure is applied in such a manner as to ensure that the at least two pads are held together. The pressure must however not be applied with a force that may lead to a decreased or blocked permeability of the sample through the pads.

With respect to the present application, there are certain precautions which may be obeyed. For instance the lamination process should only involve water in such quantities that there will be no mixing of reagents, activators, acids and/or bases from the different pads involved. This may in some cases mean that water should be totally avoided in the lamination method. The same holds true for organic solvents, which should only be used in such quantities that no mixing of reagents, activators, acids and/or bases from the different pads will take place. Furthermore, methods involving heat for conducting the lamination process have been described. Exposure to heat may deteriorate one or more of the reagents, activators, acids and/or bases and hence reduce the performance and/or stability of the dry stick. Methods involving exposure to high energy light should also be conducted in such a way that no harm will happen to the components of the dry stick.

One lamination method has proven to be particularly well suited for lamination in connection with the present application: spray gluing using organic solvent based spray glue. In particular spray glue #75 from 3M has proven to be well suited. This spray glue, which is composed of an adhesive dissolved in acetone, heptane and other organic solvents, is characterized by depositing isolated droplets of adhesive on the surface of application, leaving a relatively large proportion of the surface free of adhesive, when applying the glue in an optimal manner. It is thereby ascertained that an aqueous sample can easily penetrate from one pad to another, and good mixing of the reagents, activators, acids and/or bases involved is allowed.

Another lamination method has shown good promise as well: use of water-permeable adhesive. The water-permeable adhesive may be constructed with holes of diameters e.g. 20-400 μm or 50-200 μm may be preferred, which will allow the sample to penetrate from one pad to another, and allow for good mixing of the reagents, activators, acids and/or bases involved. In particular permeable tape from Adhesives Research Inc. has proven to be well suited.

Additional Embodiments

In an embodiment of the present invention at least one reagent pad is located relative to the regulating pad to avoid precipitation of a sample component on the top face of the device. The sample component(s) that may precipitate may be selected from the group consisting of proteins, carbohydrate, fat, cells, or other component present in the sample.

In cases where the analyte may be found in milk and where the activity is being controlled by a change in pH care should be taken if either the regulating pad or the at least one reagent pad comprises a pH-value around 5 or less. If such pad, having a pH-value around 5 or less, is placed on top of the other pads, the milk proteins may coagulate and form a precipitate on top face of the dry stick device. This precipitate may cause a decrease in the intensity of the detectable signal. Thus, it may be preferred that such pad is being location down stream from the sample-application site to avoid unwanted decrease in the detectable signal.

In an alternative embodiment of the present invention the term "top face" relates to the surface of the dry stick test device of the present invention from where the detectable signal may be obtained either by suitable instrument or apparatus or by visual inspection. This surface may be the same as the surface where the sample is applied or it may be a different surface.

Determination of LDH

As mentioned above, the inventors of the present invention have now developed a new construction of a dry stick device for the determination of the concentration of an analyte in a sample, such analyte could be lactate dehydrogenase (LDH) in body fluids. The dry stick device according to the present invention may be useful for the qualitative detection and quantitative determination of LDH in a sample wherein the test means comprises a reagent composition incorporated within a porous material.

The quantitative determination of LDH may be important for the determination of mammary inflammation which affects the integrity of mammary gland structure and concurrently damages the secretary epithelia and the blood-milk barriers. Consequently, many milk components are influenced by mastitis. Major components such as fat, protein and lactose are reduced and a number of enzymes are altered. LDH and/or N-acetyl glucosaminidase may be used as suitable indicators for the inflammation caused by mastitis. N-acetyl-β-D-glucosaminidase, also called N-acetyl glucosaminidase (NAGase), has been claimed to be one of the better markers for mammary inflammation. Furthermore, it has been shown that other enzymes in milk, like LDH may be of similar value and act as a suitable indicator of mastitis as does NAGase.

Alternatively, the quantitative determination of LDH may be extremely important in the detection of heart diseases, especially heart attacks, in that, following heart attacks, the concentration of LDH in e.g. blood rises noticeably over its normal concentration. The early detection of such an abnormal rise in LDH concentration can therefore obviously lead to a more accurate and rapid diagnosis of heart maladies.

Because early diagnosis of abnormal heart conditions is so important, a test for the detection of variables in the concentration of LDH in the blood must be rapid and simple enough for the clinician to carry out but accurate enough to enable the diagnosis to be made without extreme changes of error or false readings. Such a mechanism is represented by the novel dry stick device of the present invention. Utilizing this novel dry stick device, no instrumentation is necessary and no mixing or reconstitution of reagents is needed. Testing can therefore be conducted in the patient's home or in a doctor's office without any special equipment.

In an embodiment of the present invention a method for assaying LDH in a sample may comprise the steps of:
  (i) applying the sample suspected of containing LDH to the reagent pad
  (ii) permitting the sample to migrate into the reagent pad comprising a reagent or a combination of reagents capable of reacting with LDH, a derivative of LDH or an indicator compound for LDH to provide a detectable signal when in a moistened state, the at least one reagent pad providing a first environment for said reagent(s), first environment permitting an improved storage stability of the reagent(s) and dry stick device when in a non-moistened state
  (iii) permitting the sample to migrate from the reagent pad into a regulating pad, said regulating pad being in contact with the reagent pad, the regulating pad creating a second environment for said reagent, when in a moistened state, said second environment permitting an increased rate of reaction between LDH and the reagent(s), and
  (iv) permitting the reagent and LDH, the derivative of LDH or the indicator compound for LDH to provide a detectable signal.

In a further embodiment of the present invention the determination of LDH is based on an enzyme-based determination.

In yet an embodiment of the present invention the increased rate of reaction is provided by a change in the pH, by addition of an activator or a combination thereof. Such a change in the pH or addition of an activator has been described earlier.

The novel dry stick device for the determination of the concentration of LDH, in a sample may comprise at least one reagent pad comprising a porous material such as cellulosic paper which contains therein the dried residue resulting from the impregnation thereof with a reagent, a combination of reagents or a series of reagent materials.

The first reagent may be a tetrazolium salt. This reagent is capable of imparting to the area of the dry stick device contacted with sample a colour of such varying intensity as to be representative of the concentration of the LDH in the serum which is added to the indicator. These dyes are well known in the art and generally have the formula:

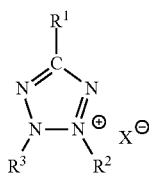

wherein $R^1$, $R^2$ and $R^3$, individually, are the same or different aryl or substituted aryl radicals and X is an anion such as a halide etc.

Examples of useful salts of this configuration include 2,3,5-Triphenyl-2H-tetrazolium chloride; 2-(p-iodophenyl)-3-(p-nitrophenyl)-5-phenyl-2H-tetrazolium chloride (INT); nitroblue tetrazolium; blue tetrazolium; and the like. These salts may be incorporated into the novel dry stick device in concentrations ranging from about 0.05 part to about 0.35 part, preferably, from about 0.1 part to about 0.2 part, based on 100 parts of solution used, in a manner set forth hereinbelow.

A second reagent that may be incorporated into the at least one reagent pad of the novel dry stick device comprises a chromatographic effect preventor which is employed in order to prevent the chromatographic movement of the tetrazolium salt over the surface of the porous material. Examples of materials which can be used for this purpose include poly (methacrylic acid), polyacrylic acid, carboxymethyl cellulose, copolymers of maleic acid and methylvinyl ether and the like. These materials are used in amounts ranging from about 0.1 part to about 3.0 parts, preferably from about 0.5 part to about 2.5 parts, based on 100 parts of solution used.

A third component to be impregnated into the at least one regent pad may be an anti-oxidant which is employed in order to prevent premature coloration of the tetrazolium salt. Examples of suitable antioxidants include the alkylated phenols such as 2,6-ditertiary butyl-p-cresol; butylated hydroxytoluene, 4-t-butyl catechol, octadecyl-3,5-di-t-butyl-4-hydroxy hydrocinnamate; alkylidene bisphenols such as 2,2'-methylenebis (6-t-butyl-4-methyl phenol), 4,4'-butylidenebis (6-t-butyl-3-methyl phenol); thiobisphenols such as 4,4'-thiobis (6-t-butyl-3-methylphenol), 2,2'-thiobis (6-t-butyl-4-methyl phenol); polyphenols such as tetrakis [methylene (3,5-di-t-butyl-4-hydroxyhydrocinnamate)]methane, 1,3,5-trimethyl-2,4,6-tris (3,5-di-t-butyl-4-hydroxybenzyl) benzene; esters such as ditridecyl thiodipropionate, distearylthiodipropionate, dilaurylthiodipropionate; amines such as diaryl or dialkyl substituted p-phenylene diamines, diphenylamine, N-phenyl-.alpha.-naphthylamine; organic phosphites such as dibutyl phosphite, didecyl phosphite, dioctyl phosphite, diphenyldecyl phosphite, ditetradecyl phosphite, phenyldidecyl phosphite, phenylneopentyl phosphite, tridecyl phosphite, trilauryl trithiophosphite, triphenyl phosphite, trisnonyl phosphite and various other well known antioxidants such as the quinones including hydroquinone, hydroquinone monomethyl ether, mono-t-butyihydroquinone, 2,5-di-t-butyl hydroquinone, toluhydroquinone, 2,5-di-t-amyl hydroquinone and the like. I may also use phenothiazine, hydroxybenzophenone, p-dimethylaminonitrosobenzene, thlodipropionic acid etc.

These anti-oxidant materials may be used in amounts ranging from about 0.01 part to 2.0 part, preferably from about 0.02 part to 1.0 part based on 100 parts of solution and may be used in conjunction with the tetrazolium salt or before or after deposition thereof.

A fourth component that may be impregnated into the at least one reagent pad may be diaphorase which is used to catalyze the reduction of the tetrazolium salt with NADH. This enzyme is well known in the art and should be employed in concentrations ranging from about 0.02 part to 0.2 part by weight and is perferably used from 0.03 part to 0.10 part based on 100 parts of solution used.

Nicotinamide-adenine-dinucleotide, hereinafter sometimes referred to as NAD, in admixture with an alkali lactate salt such as lithium lactate, sodium lactate, potassium lactate and the like, comprises a further constituent that may be impregnated into the at least one reagent pad. The use of NAD is well known in the art and should be employed in concentrations ranging from about 0.01 part to about 0.20 part and is preferably used from 0.015 part to 0.08 part by weight based on 100 parts of solution. The lactate salt is employed in amounts ranging from 0.03 part to about 1.5 parts and is preferably used from 0.02 part to 0.09 part based on 100 parts of solution used.

It is believed that the following reaction of the reagents present in the determination of LDH in a sample using the above described mechanism may be used:

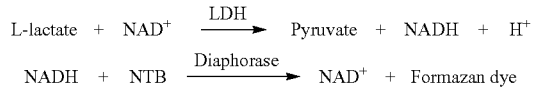

The above reaction scheme illustrates that once the sample is added to the dry stick device, the LDH therein may cause a reaction which results in the reduction of the tetrazolium salt and the formation of a colored indicator, the intensity of which is directly proportional to the concentration of the LDH. The clinician then merely compares the color which results to a standard color chart to ascertain the LDH concentration of the serum being tested.

In order to achieve optimum results utilizing the novel dry stick device of the present invention, it is also advantageous, although not necessary, to incorporate into the the at least one reagent pad a suitable non-ionic wetting agent any of those which are well-known to being applicable to the skilled artisan. For instance, fatty alkanolamides may be used, i.e. the alkanolamine reaction products with fatty acids such as lauric acid or stripped coconut fatty acid, suitable alkanolamines being diethanolamine, monoethanolamine, amonisopropanolamine and the like; ethylene oxide derived materials, i.e. those derived from the reaction of ethylene oxide with alkylphenols wherein the alkyl group is octyl, nonyl or higher, long chain fatty alcohols such as tridecyl alcohol, lanolin, lecethin alcohol etc., long chain fatty acids such as tall oil, oleic acid, abietic acid etc., long chain fatty mercaptans, long chain fatty amines, polyoxypropylene glycol, fatty sorbitan ester; sugar esters i.e. the alcoholysis reaction products of the methyl ester of a fatty acid and sucrose or raffinose; polysorbitol; polyvinyl alcohol; methyl cellulose; ethoxylated phenol/formaldehyde resins and the like. Concentrations of from about 0.01 part to about 1.0 part of wetting agent per 100 parts of solution are employed, the wetting agents preferably being added with each component, if the components are added singly or in admixture with the components if they are added as a complete admixed system.

In producing the novel dry stick device, the method employed depends primarily on the reagent which is being employed as the anti-oxidant for the tetrazolium salt. If the anti-oxidant is an organic solvent soluble only, the dry porous material, usually paper, may be impregnated with the reagents in a series of dips. Alternatively, the reagents are impregnated in two or more different reagent pads.

In an embodiment of the present invention an aqueous solution of the tetrazolium salt and optionally in combination with the chromatographic effect preventor may be prepared and the at least one reagent pad may be contacted therewith and is then dried such as in a drying tunnel or in a forced draft oven. The impregnated reagent pad or second reagent pad may then be contacted with an organic solvent solution of the anti-oxidant. The carrier is again dried. A buffer solution of diaphorase and optionally a carbohydrate stabilizer may then be prepared and one of the once impregnated, the twice impregnated or third reagent pad may be impregnated therewith and dried. A buffer solution of the NAD and alkali lactate may be prepared and one of the treated papers, or another reagent pad i.e. fourth reagent pad may by impregnated and a fourth drying completes the preparation of the test indicator In an embodiment of the present invention the method for determining LDH in a sample may be performed using a dry stick device having at least one reagent pad comprising:
  (a) a colouring compound,
  (b) diaphorase, and
  (c) a nicotinamide-dinucleotide, and
  (d) a lactate salt.

The reagents (a), (b), (c) and (d) may be in one single reagent pad or in individual reagent pads, such as in 2 different reagent pads, e.g. in 3 different reagent pads or such as in 4 different reagent pads.

In another embodiment of the present invention the dry stick device may further comprises at least one reagent pad having:
  (e) a chromatographic effect preventor, and/or
  (f) an anti-oxidant The reagents (e) and (f) may be in one single reagent pad together with reagents (a), (b), (c) and (d) or in individual reagent pads, such as in 2 different reagent pads.

The reagents may be separated into at least 2 reagent pads, such as at least 3 reagent pads, e.g. at least 4 reagent pads, such as at least 5 reagent pads, e.g. at least 6 reagent pads.

In an embodiment of the present invention the colouring compound is selected from the group consisting of tetrazolium salt or any derivative hereof If wetting agents etc. are to be incorporated, they are added during any or all of the impregnations to obtain uniform reagent deposits. Materials suitable as the carbohydrate stabilizer include maltose and sorbitol as well as water soluble polymeric ethylene oxides both high and low molecular weight, diethylene glycol and the like in concentrations ranging from about 10.0 parts to about 25.0 parts, preferably about 15.0 parts to about 20.0 parts based on 100 parts of solution used.

In an embodiment of the present invention a water-soluble anti-oxidant may be employed, and then all the reagents may be admixed together in the buffer solution the concentrations of each ingredient being as set forth above except that each is based on the same 100 parts of water, and a one dip-one dry cycle can be employed to produce the desired test indicator.

Example of buffers useful in either procedure include, phosphate buffer, phthalate buffer, tris buffer, citratephosphate buffer, borate-succinate buffer etc. The preferred buffer is tris buffer i.e. 2-amino-2-(hydroxymethyl)-1,3-propanediol in a 0.05 to 0.2M concentrations.

The color change of the test indicators prepared according to the multi-dip process may be from pink to red while the color change of the one-dip method may proceed from yellow to brown.

The above concentrations expressed in connection with the components which may be incorporated into the novel dry stick device are set forth as to the solutions of these components which are saturated onto the at least one reagent pad only and are not meant to specify the amount of each component which is eventually present on the at least one reagent pad. That is to say, saturation of the bibulous carrier with specific concentration of a specific component in solution will not unequivocally incorporate into the porous material the same amount or percentage of component present in the solution. It has been found however, that the above concentrations of solution may generally be sufficient so as to incorporate sufficient component into the at least one reagent pad upon saturation therewith to produce a functional dry stick device, the absorptive capabilities of the at least one reagent pad being characteristic of materials generally used for this purpose.

Although the above discussion with regard to the preparation of this dry stick device teaches saturation of the at least one reagent pad by dipping, it is sometimes necessary, especially wherein a series of saturations are to be conducted, to apply the component solution to the at least one reagent pad rather than dipping the carrier because extended dippings may tend to wash out previously deposited components.

It is obvious for the person skilled in the art that the first- and the second environment may be changed if a different assay for the determination of LDH is being provided. Furthermore, it is also obvious for the skilled person how to optimise the first- and the second environment based on the knowledge provided by the concept of the present invention, namely, having a first environment which may be selected in such a manner as to favour the storage of the reagent(s) capable of reacting with the analyte and providing a detectable signal and having a second environment which may be created in such a manner as to favour the performance of the reagent(s) capable of reacting with the analyte and providing a detectable signal or as to favour the rate of reaction between the analyte and the reagent(s) capable of reacting with the analyte providing a detectable signal.

In a preferred embodiment of the present invention the dry stick device is developed to measure LDH in accordance with the above mentioned reaction scheme for detecting LDH. In this construction it may be preferred that the at least one reagent pad is provided with a pH-value of approximately pH 6.8 and the regulation pad is provided with a pH-regulating agent capable of providing a second environment for the reagent or the combination of reagents of approximately pH 8.3.

Determination of β-hydroxybutyrate (BNB)

BHB is being formed when fat is mobilised for energy. The level of BHB, with other ketone bodies, increases during hunger or with underfeeding, of e.g. animals. The level is closely related to energy status when there is a high demand for glucose, i.e. during late pregnancy and lactation of herd animals, such as cows.

In an embodiment of the present invention the determination of BHB may be performed using the same reaction scheme as provided for the determination of LDH as provided above.

In a preferred embodiment of the present invention the dry stick device is developed to measure BHB in accordance with the above mentioned reaction scheme for detecting BHB. In this construction it may be preferred that the at least one reagent pad is provided with a pH-value of approximately pH 6.8 and the regulation pad is provided with an pH-regulating agent capable of providing a second environment for the reagent or the combination of reagents of approximately pH 8.3.

Determination of Urea

Determination of protein utilisation may be an important parameter. In cattle farming, it is highly important that the animals (e.g. cows) optimally utilize the protein contained in the feed, because protein is one of the most expensive feed components. The utilization depends, Inter alia, on the amount of energy and protein simultaneously present in the animal.

In an embodiment of the present invention the determination of urea may be performed using the following reaction scheme:

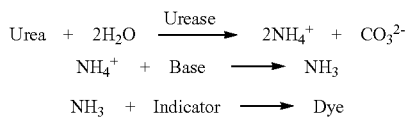

In a preferred embodiment of the present invention the dry stick device is developed to measure BHB in accordance with the above mentioned reaction scheme for detecting BHB. In this construction, and when using urease obtained from Jack Beans, it may be preferred that the at least one reagent pad is provided with a pH-value of approximately pH 8.0 and the regulation pad is provided with a pH-regulating agent capable of providing a second environment for the reagent or the combination of reagents of approximately pH 6.0.

Determination of N-Acetyl Glucosaminidase (NAGase)

The quantitative determination of NAGase may in the same way as LDH be important for the determination of mammary inflammation which affects the integrity of mammary gland structure and concurrently damages the secretary epithelia and the blood-milk barriers.

In an embodiment of the present invention the determination of urea may be performed using the following reaction scheme:

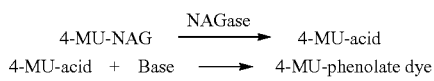

Here 4-MU-NAG relates to 4-methylumbelliferyl N-acetyl-beta-D-glucosaminide, 4-MU-acid relates to 4-methylumbelliferone and 4-MU-phenolate dye relates to a 4-methylumbelliferone salt.

In a preferred embodiment of the present invention the dry stick device is developed to measure NAGase in accordance with the above mentioned reaction scheme for detecting NAGase. In this construction it may be preferred that the at least one reagent pad is provided with a pH-value of approximately pH 7.0 and the regulation pad is provided with an pH-regulating agent capable of providing a second environment for the reagent or the combination of reagents of approximately pH 4.6.

It is obvious for the person skilled in the art that the first- and the second environment may be changed if a different assay for the determination of LDH, BHB, urea, NAGase or any other analyte is being provided. Furthermore, it is also obvious for the skilled person how to optimise the first- and the second environment based on the knowledge provided by the concept of the present invention, namely, having a first environment which may be created in such a manner as to favour the storage of the reagent(s) capable of reacting with the analyte and providing a detectable signal and having a second environment which may be created in such a manner as to favour the performance of the reagent(s) capable of reacting with the analyte and providing a detectable signal or as to favour the rate of reaction between the analyte and the reagent(s) capable of reacting with the analyte providing a detectable signal.

The concept of the present invention will be further illustrated in the following non-limiting examples.

EXAMPLES

Example 1

Preparation and Test of LDH Dry Sticks

Type 1a, single layer construction, pH 6.8
Preparation of Impregnation Solution:

1.5 g of lithium L-lactate, 3.0 g of β-NAD$^+$, 150 mg of polyethylene glycol 20,000, and 1.5 g sucrose are dissolved in 120 mL of 0.1 M phosphate buffer pH 8.0. Then 1.5 mL of 5% solution of Triton X-100 is added, followed by 1.5 g of bovine serum albumin (BSA), 30 KU of diaphorase, and 150 mg of nitro blue tetrazolium (NTB). 0.1 M phosphate buffer pH 8.0 is added to make 150 mL in total and the solution is stirred. The final pH of this solution is pH 6.8.

Paper Impregnation:

The impregnation solution is transferred to a stainless steel vat. One sheet of filter paper 20×20 cm (e.g. Whatman 3MMChr) is impregnated in the impregnation solution pH 6.8 for about 10 seconds. Then the filter paper is removed from the impregnation solution and allowed to drain off by holding the paper vertically for about 30 seconds by using a clean clip. 10 or 11 sheets may be impregnated in total.

Drying:

The sheets of impregnated filter paper are dried in a well ventilated oven at 38-42° C. until they are dry (approx. 45 minutes). The dried filter papers may be kept in sealed foil bags with a drying agent at about 4-6° C. until use.

Cutting:

The impregnated sheet is cut into 5 mm wide strips e.g. in a rotary cutter, and then the strips are cut into 5 mm×5 mm squares by cutting the strips orthogonally e.g. in a rotary cutter.

Type 1b, single layer construction, pH 8.3
Preparation of Impregnation Solution:

1.5 g of lithium L-lactate, 3.0 g of β-NAD$^+$, 150 mg of polyethylene glycol 20,000, and 1.5 g sucrose are dissolved in 120 mL of 0.1 M Tris-HCl buffer pH 9.0. Then 1.5 mL of 5% solution of Triton X-100 is added, followed by 1.5 g of bovine serum albumin (BSA), 30 KU of diaphorase, and 150 mg of nitro blue tetrazolium (NTB). 0.1 M Tris-HCl buffer pH 9.0 is added to make 150 mL in total and the solution is stirred. The final pH of this solution is pH 8.3.

Paper Impregnation:

The impregnation solution is transferred to a stainless steel vat. One sheet of filter paper 20×20 cm (e.g. Whatman 3MMChr) is impregnated in the impregnation solution pH 8.3 for about 10 seconds. Then the filter paper is removed from the impregnation solution and allowed to drain off by holding the paper vertically for about 30 seconds by using a clean clip. 10 or 11 sheets may be impregnated in total.

Drying:

The sheets of impregnated filter paper are dried in a well ventilated oven at 38-42° C. until they are dry (approx. 45 minutes). The dried filter papers may be kept in sealed foil bags with a drying agent at about 4-6° C. until use.

Cutting:

The impregnated sheet is cut into 5 mm wide strips e.g. in a rotary cutter, and then the strips are cut into 5 mm×5 mm squares by cutting the strips orthogonally e.g. in a rotary cutter.

Type 2, double layer construction, pH 6.8 in reagent pad, pH~12 in regulation pad Preparation of Impregnation Solution for Reagent Pad (pH 6.8):

1.5 g of lithium L-lactate, 3.0 g of β-NAD$^+$, 150 mg of polyethylene glycol 20,000, and 1.5 g sucrose are dissolved in 120 mL of 0.1 M phosphate buffer pH 8.0. Then 1.5 mL of 5% solution of Triton X-100 is added, followed by 1.5 g of bovine serum albumin (BSA), 30 KU of diaphorase, and 150 mg of nitro blue tetrazolium (NTB). 0.1 M phosphate buffer pH 8.0 is added to make 150 mL in total and the solution is stirred. The final pH of this solution is pH 6.8.

Impregnation of the Reagent Pad:

The impregnation solution is transferred to a stainless steel vat. One sheet of filter paper 20×20 cm (e.g. Whatman 3MMChr) is impregnated in the impregnation solution pH 6.8 for about 10 seconds. Then the reagent pad is removed from the impregnation solution and allowed to drain of by holding the paper vertically for about 30 seconds by using a clean clip. 10 or 11 sheets may be impregnated in total.

Drying of the Reagent Pad:

The sheets of impregnated reagent pad are dried in a well ventilated oven at 38-42° C. until they are dry (approx. 45 minutes). The dried reagent pads may be kept in sealed foil bags with a drying agent at about 4-6° C. until use.

Preparation of Impregnation Solution for Regulation Pad (pH 12):

50 g of TRIS (2-amino-2-(hydroxymethyl)-1,3-propanediol) are dissolved in 200 mL of deionised water to afford a solution with pH~12.

Impregnation of the regulation Pad:

The impregnation solution is transferred to a plastic vat. One sheet of wiper 10×20 cm (e.g. Asahi Bemcot PS-2) is impregnated in the impregnation solution pH~12 for about 30 seconds. Then the regulation pad is removed from the impregnation solution and placed flat on a stainless steel mesh tray. Approximately 25 sheets of regulation pads may be impregnated in total.

Drying of the Regulation Pad:

The regulation pads are dried in a well ventilated oven at 38-42° C. until they are dry (approx. 10 minutes). The dried wipers may be stored in sealed foil bags with a drying agent at about 4-6° C. until use.

Lamination of Impregnated Reagent Pad pH 6.8 and Impregnated Regulation Pad pH~12:

A thin film of spray glue (e.g. 3M #75) is applied to one side of the impregnated regulation pad. A cut sheet 10×20 cm of impregnated reagent pad is placed on a flat clean surface and the sheet of spray glued regulation pad is placed on top of the reagent pad, and the two layers are laminated together by applying pressure from a rubber roller. The edges of the laminated sheet are trimmed to get rid of non-laminated material. The laminated sheets may be stored in sealed foil bags with a drying agent at about 4-6° C. until use.

Cutting:

The laminated sheet is cut into 5 mm wide strips e.g. in a rotary cutter, and then the strips are cut into 5 mm×5 mm squares by cutting the strips orthogonally e.g. in a rotary cutter. The squares are sorted such that the filter paper side is on top.

Performance Test of LDH Stick Types 1a, 1b, and 2

The performance test was carried out in the following way: A calibration series of LDH in milk was prepared fresh by spiking UHT milk with 0, 100, 500, and 1000 U/L of LDH enzyme (Sigma #L1378 from bovine muscle). 10 μL of milk from the calibration series were added to one stick at 25° C., which was then incubated at 25° C. for 5 minutes. The colour development on the stick was assessed by use of a spectrophotometer, at a wavelength of 520 nm.

The experimental results from measurement with stick types 1a, 1b, and 2 are shown in Table 1.

TABLE 1

Calibration curves with stick types 1a, 1b, and 2.

| LDH (U/L) | Type 1a | Type 1b | Type 2 |
|---|---|---|---|
| pH | 6.8 | 8.3 | "6.8 comb. 12 -> 8.3" (See example 3 below) |
| 0 | 0.78 | 0.76 | 0.77 |
| 100 | 0.72 | 0.57 | 0.58 |
| 500 | 0.67 | 0.42 | 0.41 |
| 1000 | 0.60 | 0.34 | 0.33 |

Stick type 1a, which was impregnated at pH 6.8, gives rise to a relatively shallow calibration curve, where the dynamic range spans 0.18. Stick type 1b, which was impregnated at pH 8.3, gives rise to a relatively steep calibration curve, where the dynamic range spans 0.42. Stick type 2, which is constructed by a reagent pad impregnated at pH 6.8 combined with a regulation pad impregnated at pH 12, gives rise to a relatively steep calibration curve quite similar to that of type 1b, where the dynamic range spans 0.44.

Accelerated stability test of LDH stick types 1a, 1b, and 2

An accelerated stability test was carried out by storing sticks of the three types 1a, 1b, and 2, respectively, in closed foil bags with drying agent at 37° C. for 1 week. After this time a performance test as described above was carried out. It is generally accepted that if performance does not change after one week at 37° C. in closed foil bags, sticks may have a storage time of at least 12 months at 4° C. in closed foil bags. Therefore, an accelerated stability test gives a good indication of the real long term stability of the tested material.

The experimental results obtained with stick types 1a, 1b, and 2, respectively, are shown in Table 2.

TABLE 2

Accelerated stability of stick types 1a, 1b, and 2.

| LDH (U/L) | Type 1a | Type 1b | Type 2 |
|---|---|---|---|
| pH | 6.8 | 8.3 | "6.8 comb. 12 -> 8.3" (See example 3 below) |
| 0 | 0.77 | 0.63 | 0.77 |
| 100 | 0.72 | 0.54 | 0.57 |

TABLE 2-continued

Accelerated stability of stick types 1a, 1b, and 2.

| LDH (U/L) | Type 1a | Type 1b | Type 2 |
|---|---|---|---|
| 500 | 0.68 | 0.42 | 0.41 |
| 1000 | 0.60 | 0.35 | 0.33 |

Stick type 1a, which was impregnated at pH 6.8, gives practically the same performance curve after 1 week of accelerated aging, as before. Stick type 1b, which was impregnated at pH 8.3, shows a much more shallow calibration curve after 1 week of accelerated aging, as compared to the same type of sticks without accelerated aging. Stick type 2, which is constructed by a reagent pad impregnated at pH 6.8 combined with a regulation pad impregnated at pH 12, gives practically the same performance curve after 1 week of accelerated aging, as before.

Stick type 2 thus shows the same good performance as stick type 1b and the same good storage stability as stick type 1a.

Example 2

Selection of Optimum pH with Respect to Performance and Stability, Respectively a. One-Layer Stick Construction for Measurement of LDH: pH Variation of Impregnation Liquid.

Test 1 (phosphate buffer, final pH 6.81):

Impregnation liquid was prepared from 100 mM phosphate buffer (pH 8.0), lactate (10 mg/mL), NAD+ (20 mg/mL), diaphorase (200 U/mL), and NTB (2 mg/mL) to give a final pH of 6.81. Whatman paper 3MMChr was impregnated and dried in an oven at 40° C. for 1 hour. Squares of 5×5 mm were cut from the impregnated paper and mounted in plastic housings.

Test 2 (TRIS buffer, final pH 8.18):

Impregnation liquid was prepared from 100 mM TRIS buffer (pH 9.0), lactate (10 mg/mL), NAD+ (20 mg/mL), diaphorase (200 U/mL), and NTB (2 mg/mL) to give a final pH of 8.18. Whatman paper 3MMChr was impregnated and dried in an oven at 40° C. for 1 hour. Squares of 5×5 mm were cut from the impregnated paper and mounted in plastic housings.

LDH standard series: LDH panels were prepared from Sigma LDH (L-2525) in UHT milk with the following activities: 0 U/L, 100 U/L, 500 U/L, and 1000 U/L.

The sticks were tested by adding 8 µL of LDH standard at 25° C. Incubation time: 5 minutes.

Stick Performance Results:

The performance results are presented in Table 1.

TABLE 1

Performance investigation of tests 1 and 2.

| Test | Reflectance % | | | | |
|---|---|---|---|---|---|
| | 0 U/L | 100 U/L | 500 U/L | 1000 U/L | $\Delta_{0-1000}$ |
| #1, pH 6.81 | 80 | 76 | 67 | 60 | 20 |
| #2, pH 8.18 | 65 | 57 | 42 | 35 | 30 |

The results show that the reflectance difference over the range 0-1000 U/L is significantly higher with sticks prepared at pH 8.18 in TRIS buffer than with sticks prepared at pH 6.81 in phosphate buffer. This means that the sensitivity is higher with sticks prepared at pH 8.18 in TRIS buffer than with sticks prepared at pH 6.81 in phosphate buffer.

Stick Stability Results:

Sticks were kept in sealed foil bags with drying agent at 4, 30, and 37° C., respectively, for 1 week. The sticks were then tested as described above, and the results are presented in Table 2.

TABLE 2

Test of sticks from stability investigation of tests 1 and 2.

| Experiment | Storage temp. ° C. | Reflectance % | | | |
|---|---|---|---|---|---|
| | | 0 U/L | 100 U/L | 500 U/L | 1000 U/L |
| #1, pH 6.81 | 4 | 78.8 | 77.3 | 69.5 | 63.1 |
| | 30 | 77.7 | 76.3 | 69.0 | 62.8 |
| | 37 | 77.1 | 73.8 | 67.4 | 59.9 |
| #2, pH 8.18 | 4 | 64.4 | 58.0 | 43.1 | 36.1 |
| | 30 | 59.6 | 54.8 | 41.5 | 34.7 |
| | 37 | 53.1 | 48.8 | 38.8 | 33.9 |

Sticks prepared at pH 6.81 in phosphate buffer show only minor displacement when going from 4 to 30 and further on to 37° C. In contrast, sticks prepared at pH 8.18 in TRIS buffer show significant decrease of reflectance values in the low LDH activity end of the range. The results show that the stability of sticks prepared at pH 6.81 in phosphate buffer is significantly better than of sticks prepared at pH 8.18 in TRIS buffer.

b. One-Layer Stick Construction for Measurement of LDH; pH Variation of LDH Sample.

Test 3 (pH adjustment carried out by using TRIS buffer):

Sticks were prepared according to the recipe in Test 1 above.

LDH Standard Series in Milk:

0 U/L-series: A standard series of UHT milk without any LDH added, but with pH adjusted at discrete values in the range 6.55 to 8.84, was prepared by mixing UHT milk with UHT milk doped with TRIS buffer (100 mM). The discrete pH values are: 6.55, 7.20, 7.83, 8.13, 8.33, 8.44, 8.57, 8.64, 8.72, 8.77, and 8.84.

175 U/L-series: A standard series of UHT milk with 175 U/L LDH added, and with pH adjusted at discrete values in the range 6.55 to 8.84, was prepared by mixing UHT milk containing 175 mM LDH with UHT milk containing 175 mM LDH and doped with TRIS buffer (100 mM). The discrete pH values are as given above.

350 U/L-series: A standard series of UHT milk with 350 U/L LDH added, and with pH adjusted at discrete values in the range 6.55 to 8.84, was prepared by mixing UHT milk containing 350 mM LDH with UHT milk containing 350 mM LDH and doped with TRIS buffer (100 mM). The discrete pH values are as given above.

The sticks were tested by adding 10 μL of LDH standard at 25° C. Incubation time: 5 minutes.

Stick Performance Results:

The performance results are presented in Table 3.

TABLE 3

Test of sticks with LDH in milk samples adjusted at various pH values by using TRIS buffer.

| Test | Reflectance % | | | |
|---|---|---|---|---|
| | 0 U/L | 175 U/L | 350 U/L | $\Delta_{0\text{-}350}$ |
| 3A, pH 6.55 | 73.7 | 58.0 | 49.4 | 24.3 |
| 3B, pH 7.20 | 73.3 | 55.0 | 46.5 | 26.8 |
| 3C, pH 7.83 | 74.0 | 50.1 | 44.6 | 29.4 |
| 3D, pH 8.13 | 71.7 | 46.8 | 38.8 | 32.9 |
| 3E, pH 8.33 | 71.6 | 41.7 | 33.8 | 37.8 |
| 3F, pH 8.44 | 71.1 | 35.4 | 29.8 | 41.3 |
| 3G, pH 8.57 | 68.9 | 34.1 | 27.4 | 41.5 |
| 3H, pH 8.64 | 68.2 | 32.5 | 27.1 | 41.1 |
| 3I, pH 8.72 | 68.7 | 31.9 | 26.0 | 42.7 |
| 3J, pH 8.77 | 66.0 | 31.7 | 24.6 | 41.4 |
| 3K, pH 8.84 | 68.0 | 31.4 | 24.6 | 43.4 |

The results show that performance improves with increasing pH values of the LDH in milk samples. The performance improvement tends to level off at a pH value around 8.4

Conclusion:

These tests demonstrate that the best pH conditions for optimal performance for the determination of LDH under the present conditions are using the TRIS-buffer at pH about 8.18 at which condition the storage stability turned out to be bad. On the other hand, to improve storage stability the pH value should be decreased and it was shown that pH about 6.81 is significantly better that the storage stability provided at pH 8.18.

Thus, the initial pH value of the regulating pad may be determined by trial and error tests which, when combined with the pH-value (pH 6.81) providing an improved storage stability, will provide the optimum (or close to the optimum) performance of the stick.

Furthermore, it is also demonstrated that the present invention provides a stable system or dry stick device where minor deviations from the optimal pH value of the regulating pad have limited or no effect on the performance of the dry stick device, which appears from test 3F to 3K.

References

U.S. Pat. No. 3,867,259 (by Forgione)

Lippenheide et al. (1995)

U.S. Pat. No. 4,215,995

Trevor Palmer, 2. edition, "Understanding Enzymes" published in 1985

The invention claimed is:

1. A dry stick device for the determination of an analyte in a sample, said device comprises:
   (i) a solid support,
   (ii) at least one reagent pad comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device when in a non-moistened state,
   (iii) a regulating pad being in contact with the at least one reagent pad, the regulating pad creating a second environment for said reagent(s) when in a moistened state, said second environment permitting an increased rate of reaction between the analyte and the reagent(s), and
   wherein the sample is applied to one surface of the dry stick device and the detectable signal is detected on the same surface.

2. A device according to claim 1, wherein the determination of the analyte is based on an enzyme-based determination.

3. A device according to claim 1, wherein the increased rate of reaction is provided by an activator, a change in pH by the addition of an acid, a base or a combination thereof.

4. A device according to claim 3, wherein the activator is a metal ion.

5. A device according to claim 4, wherein the activator is a cation selected from the group consisting of $Na^+$, $K^+$, $Ca^{2+}$, $Mg^{2+}$, $Cu^{2+}$, $Fe^{2+}$, $Fe^{2+}$, $Zn^{2+}$, $Mn^{2+}$ and any combination thereof.

6. A device according to claim 3, wherein the activator is an anion selected from the group consisting of acetates, sulfates, carbonates, chlorides and nitrates.

7. A device according to claim 1, wherein the device comprises at least two reagent pads.

8. A device according to claim 1, wherein the regulating pad is in contact with the at least one reagent pad by substantially fully overlapping, by partially overlapping or by laying adjacent to at least one reagent environment.

9. A device according to claim 1, wherein the at least one reagent pad and the regulating pad comprise a porous material.

10. A device according to claim 9, wherein the porous material is selected from the group consisting of a nitrocellulose membrane, a cellulose, a polymer, glass fibres, woven fibres, non-woven fibres and a chromatographic gel membrane.

11. A device according to claim 1, wherein at least one reagent pad and/or the regulating pad incorporate at least one ancillary compound capable of improving the flow of the sample.

12. A device according to claim 11, wherein the ancillary compound is a liquid.

13. A device according to claim 11, wherein the ancillary compound provides a fast, consistent and homogenous release of the reagent(s) in the at least one reagent pad and/or the agent in the regulating pad.

14. A device according to claim 11, wherein the ancillary compound provides low affinity for protein binding.

15. A device according to claim 11, wherein the ancillary compound provides low retention of triglyceride rich samples.

16. A device according to claim 11, wherein the ancillary compound decreases the viscosity of the sample.

17. A device according to claim 11, wherein the ancillary compound contains chemical constituents selected from the group consisting of water, a surfactant, a salt, a metal, a sugar, a protein and a lipid.

18. A device according to claim 1, wherein the solid support is selected from the group consisting of tubes, polymeric beads, nitrocellulose strips, membranes, filters and plastic sheets.

19. A device according to claim 1, wherein the analyte is selected from the group consisting of a protein, an enzyme, a fat, a carbohydrate, an antibiotic, a steroid, a vitamin, a chemical compound and a cell.

20. A device according to claim 19, wherein the enzyme is selected from the group consisting of catalase, lactate dehydrogenase (LDH), alkaline phosphatase, acid phosphatase, carboxylesterase, arylesterase,β-glucuronidase, lactoperoxidase, lipase, lysozyme, xanthine oxidase, plasmin and beta-N-acetylhexosaminidase (NAGase) and prostaglandin D synthase (PGDS).

21. A device according to claim 19, wherein the chemical compound is selected from the group consisting of urea, triglycerid, ketone bodies, and steroids.

22. A device according to claim 19, wherein the carbohydrate is selected from the group consisting of a monosaccharide, and a disaccharide.

23. A device according to claim 1, wherein the sample is collected from a mammal.

24. A device according to claim 23 wherein the mammal is selected from the group consisting of herd animals, cows, camels, buffaloes, pigs, horses, deer, sheep, goats, pets, dogs, cats and humans.

25. A device according to claim 1, wherein at least one reagent pad is located relative to the regulating pad to avoid precipitation of a sample component on the top face of the device.

26. A device according to claim 25, wherein the sample component is selected from the group consisting of proteins, carbohydrates, fats and cells present in the sample.

27. A device according to claim 1, wherein the first environment is created in such a manner as to favour the storage stability of the reagent(s) capable of reacting with the analyte and providing a detectable signal.

28. A device according to claim 1, wherein the second environment is created in such a manner as to favour the performance of the reagent(s) capable of reacting with the analyte and providing a detectable signal.

29. A device according to claim 1, wherein the second environment is created in such a manner as to favour the rate of reaction between the analyte and the reagent(s) capable of reacting with the analyte providing a detectable signal.

30. A dry stick device according to claim 1 having at least two laminated pads.

31. A dry stick device according to claim 30, wherein said laminated pads are laminated by gluing, sewing, pressing or any combination hereof.

32. A method for assaying an analyte in a milk sample, said method comprises the steps of:
(i) applying the milk sample suspected of containing the analyte to a reagent pad,
(ii) permitting the sample to migrate into the reagent pad comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device when in a nonmoistened state,
(iii) permitting the sample, alone or together with the reagent, to migrate from the reagent pad into a regulating pad, said regulating pad being in contact with the reagent pad, the regulating pad creating a second environment for said reagent when in a moistened state, said second environment permitting an increased rate of reaction between the analyte and the reagent(s),
(iv) permitting the reagent and the analyte, the derivative of said analyte or the indicator compound for said analyte to provide a detectable signal, and
(v) detecting the detectable signal on the same surface at which the sample was applied.

33. A method according to claim 32, wherein the increased rate of reaction is provided by an activator, a change in pH by addition of an acid, a base or any combination thereof.

34. A method according to claim 33, wherein the activator is a metal ion.

35. A method according to claim 34, wherein the activator is a cation selected from the group consisting of $Na^+$, $K^+$, $Ca^{2+}$, $Mg^{2+}$, $Cu^{2+}$, $Fe^{2+}$, $Fe^{3+}$, $Zn^{2+}$, $Mn^{2+}$ and any combination thereof.

36. A method according to claim 32, wherein the device comprises at least two reagent pads.

37. A method according to claim 32, wherein the regulating pad is in contact with at least one reagent pad by substantially fully overlapping, by partially overlapping or by laying adjacent to at least one reagent pad.

38. A method according to claim 32, wherein the analyte is selected from the group consisting of a protein, an enzyme, a fat, a carbohydrate, an antibiotic, a drug of abuse, a steroid, a vitamin, a chemical compound and a cell.

39. A method according to claim 38, wherein the enzyme is selected from the group consisting of catalase, lactate dehydrogenase (LDH), alkaline phosphatase, acid phosphatase, carboxylesterase, arylesterase, β-glucuronidase, lactoperoxidase, lipase, lysozyme, xanthine oxidase, plasmin and beta-N-acetylhexosaminidase (NAGase) and prostaglandin D synthase (PGDS).

40. A method according to claim 38, wherein the chemical compound is selected from the group consisting of urea, triglycerid, ketone bodies and steroids.

41. A method according to claim 38, wherein the carbohydrate is selected from the group consisting of a monosaccharide and a disaccharide.

42. A method according to claim 32, wherein the sample is collected from a mammal.

43. A method according to claim 42, wherein the mammal is selected from the group consisting of herd animals, cows, camels, buffaloes, pigs, horses, deer, sheep, goats, pets, dogs, cats and humans.

44. A method according to claim 32, wherein the first environment is created in such a manner as to favour the storage of the reagent(s) capable of reacting with the analyte and providing a detectable signal.

45. A method according to claim 32, wherein the second environment is created in such a manner as to favour the performance of the reagent(s) capable of reacting with the analyte and providing a detectable signal.

46. A method according to claim 32, wherein the second environment is created in such a manner as to favour the rate of reaction between the analyte and the reagent(s) capable of reacting with the analyte providing a detectable signal.

47. A method according to claim 32, wherein the dry stick device has at least two laminated pads.

48. A method according to claim 47, wherein said laminated pads are laminated by gluing, sewing, pressing or any combination hereof.

49. A method for the preparation of the dry stick device according to claim 1, said method consisting essentially of the steps:
(i) providing a reagent pad by impregnating a first porous material with an aqueous solution comprising a reagent or a combination of reagents capable of reacting with the analyte, a derivative of said analyte or an indicator compound for said analyte to provide a detectable signal when in a moistened state, the at least one reagent pad providing a first environment for said reagent(s), said first environment permitting an improved storage stability of the reagent(s) and dry stick device,
(ii) thereafter drying the reagent pad,
(iii) providing a regulating pad by impregnating a second porous material with an aqueous solution creating a second environment for said reagent(s) when in a moistened state, said second environment permitting an increased rate of reaction between the analyte and the reagent, (iv) thereafter drying the impregnated second porous material, and (v) contacting the reagent pad with the regulating pad, optionally on a solid support, to obtain the dry stick device, wherein these steps result in the preparation of a dry stick device configured to receive the sample on one surface of the dry stick device and detect the detectable signal on the same surface.

50. A method according to claim 49, wherein the device comprises at least two reagent pads.

51. A method according to claim 49, wherein the regulating pad is in contact with at least one reagent pad by substantially fully overlapping, by partially overlapping or by laying adjacent to at least one reagent pad.

52. A method according to claim 49, wherein the porous material is selected from the group consisting of a nitrocellulose membrane, a cellulose, a polymer, glass fibres, woven fibres, non-woven fibres and a chromatographic gel membrane.

53. A method according to claim 49, wherein the solid support is selected from the group consisting of tubes, polymeric beads, nitrocellulose strips, membranes, filters and plastic sheets.

54. A method according to claim 49, wherein at least one reagent pad is located relative to the regulating pad to avoid precipitation of a sample component on the top face of the device.

55. A method according to claim 54, wherein the sample component is selected from the group consisting of proteins, carbohydrates, fats and cells present in the sample.

56. A method according to claim 49, wherein the first environment is selected in such a manner as to favour the storage of the reagent(s) capable of reacting with the analyte and providing a detectable signal.

57. A method according to claim 49, wherein the second environment is selected in such a manner as to favour the performance of the reagent(s) capable of reacting with the analyte and providing a detectable signal.

58. A method according to claim 49, wherein the second environment is selected in such a manner as to favour the rate of reaction between the analyte and the reagent(s) capable of reacting with the analyte providing a detectable signal.

59. A method according to claim 49, wherein the dry stick device has at least two laminated pads.

60. A method according to claim 59, wherein said laminated pads are laminated by gluing, sewing, pressing or any combination hereof.

61. A device according to claim 3, wherein the activator is a mono-, di- or trivalent metal ion.

62. A device according to claim 10, wherein the polymer is selected from the group consisting of nylon, polyvinylidene fluoride and latex.

63. A device according to claim 19, wherein the cell is selected from the group consisting of a leukocyte and blood.

64. A device according to claim 21, wherein the ketone body is selected from the group consisting of acetoacetate, beta-hydroxybutyrate (BOHB), acetone, ascorbic acid, nitrates, urobilinogen and cholesterol.

65. A device according to claim 21, wherein the steroid is selected from the group consisting of pregnenolone, progesterone, testosterone, dihydrotestosterone, estrone, estradiol, cortisol, cortisone, aldosterone, corticosterone, androstenedione, 17α-OH-pregnenolone, 17α-OH-progesterone, 11-desoxy-corticosterone, 11-desoxycortisol and dehydroepiandrosterone, luteinising hormone and human chorionic gonadotropin.

66. A device according to claim 22, wherein the monosaccharide is selected from the group consisting of glucose and galactose.

67. A device according to claim 22, wherein the disaccharide is lactose.

68. A method according to claim 34, wherein the metal ion is a mono-, di- or trivalent metal ion.

69. A method according to claim 38, wherein the cell is selected from the group consisting of a leukocyte and blood.

70. A method according to claim 40, wherein the ketone body is selected from the group consisting of acetoacetate, beta-hydroxybutyrate (BOHB), acetone, ascorbic acid, nitrates, urobilinogen and cholesterol.

71. A method according to claim 40, wherein the steroid is selected from the group consisting of pregnenolone, progesterone, testosterone, dihydrotestosterone, estrone, estradiol, cortisol, cortisone, aldosterone, corticosterone, androstenedione, 17α-OH-pregnenolone, 17α-OH-progesterone, 11-desoxy-corticosterone, 11-desoxycortisol and dehydroepiandrosterone, luteinising hormone and human chorionic gonadotropin.

72. A method according to claim 41, wherein the monosaccharide is selected from the group consisting of glucose and galactose.

73. A method according to claim 41, wherein the disaccharide is lactose.

74. A method according to claim 52, wherein the polymer is selected from the group consisting of nylon, polyvinylidene fluoride and latex.

75. A dry stick according to claim 31, wherein a glue is selected from the group consisting of spray glue, aerosol glue and tape.

76. A method according to claim 48, wherein a glue is selected from the group consisting of spray glue, aerosol glue and tape.

77. A method according to claim 59, wherein a glue is selected from the group consisting of spray glue, aerosol glue and tape.

* * * * *